US011389667B2

(12) United States Patent
Da Silva Rodrigues et al.

(10) Patent No.: US 11,389,667 B2
(45) Date of Patent: Jul. 19, 2022

(54) METHODS AND APPARATUS FOR REDUCING RISK TO A SUBJECT UNDERGOING RADIOTHERAPY-BASED TREATMENT

(71) Applicant: KONINKLIJKE PHILIPS N.V., Eindhoven (NL)

(72) Inventors: Pedro Jorge Da Silva Rodrigues, Veldhoven (NL); Alfonso Agatino Isola, Eindhoven (NL); Reinhold Wimberger-Friedl, Waalre (NL); Vanda Lucia de Carvalho Vittorino De Almeida, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 16/770,691

(22) PCT Filed: Dec. 18, 2018

(86) PCT No.: PCT/EP2018/085377
§ 371 (c)(1),
(2) Date: Jun. 8, 2020

(87) PCT Pub. No.: WO2019/121604
PCT Pub. Date: Jun. 27, 2019

(65) Prior Publication Data
US 2021/0162233 A1 Jun. 3, 2021

(30) Foreign Application Priority Data
Dec. 21, 2017 (EP) .................................... 17209220

(51) Int. Cl.
*A61N 5/10* (2006.01)
*G16H 20/40* (2018.01)
*G16H 50/30* (2018.01)

(52) U.S. Cl.
CPC ........... *A61N 5/1031* (2013.01); *G16H 20/40* (2018.01); *G16H 50/30* (2018.01)

(58) Field of Classification Search
CPC .. A61B 6/00; A61B 6/46; A61B 6/461; A61B 6/467; A61B 6/468; A61B 6/50;
(Continued)

(56) References Cited

U.S. PATENT DOCUMENTS

| 9,764,162 B1 | 9/2017 | Willcut |
| 2004/0131587 A1 | 7/2004 | Thomas |

(Continued)

FOREIGN PATENT DOCUMENTS

| WO | 2016065330 A1 | 4/2016 |
| WO | 2016164665 A1 | 10/2016 |
| WO | 2017027879 A1 | 2/2017 |

OTHER PUBLICATIONS

International Search Report and Written Opinion of PCT/EP2018/085377, dated Apr. 8, 2019.
(Continued)

*Primary Examiner* — Don K Wong

(57) ABSTRACT

A method of generating a strategy for performing a radiotherapy-based treatment and a system for performing the method. During a radiotherapy-based treatment, characteristics of side-effects are monitored and a risk model of the subject modified based on the characteristics. A new treatment strategy for the radiotherapy-based treatment is obtained based on the modified risk model.

15 Claims, 5 Drawing Sheets

(58) Field of Classification Search
CPC ....... A61B 6/52; A61B 6/5211; A61B 6/5217;
A61B 6/5294; A61B 6/54; A61B 5/00;
A61B 5/0002; A61B 5/48; A61B 5/4836;
A61B 5/4842; A61B 5/4848; A61B 5/74;
A61B 5/742; A61B 5/7435; A61B 5/743;
A61B 2576/00; A61N 5/1031; A61N
5/1048; A61N 5/1049; A61N 5/1064
See application file for complete search history.

(56) References Cited

U.S. PATENT DOCUMENTS

| | | |
|---|---|---|
| 2012/0004492 A1 | 1/2012 | Weibrecht |
| 2012/0063657 A1 | 3/2012 | Ribbing |
| 2014/0095201 A1 | 4/2014 | Farooq |
| 2016/0117443 A1* | 4/2016 | Van Ooijen ............ G16B 25/10 514/249 |
| 2017/0083682 A1 | 3/2017 | McNutt |
| 2017/0199979 A1 | 7/2017 | Reiner |

OTHER PUBLICATIONS

Teng, Feifei et al "Radiotherapy combined with Immune Checkpoint Blockage Immunotherapy: Achievements and Challenges", Cander Letters, vol. 365, No. 1, May 2015, pp. 23-29.

Kyi, Chrisann et al "Immune Checkpoint Inhibitor combinations in Solid Tumors: Opportunities and Challenges", Immunotheraphy, vol. 8, No. 7, 2016, pp. 821-837.

Spiotto, Michael et al "The Intersection of Radiotherapy and Immunotherapy: Mechanisms and Clinical Implications", Science Immunol., vol. 1, No. 3, 2016.

Bernier, Jacques, "Allying forces of radio- and immuno-therapy to enhance cancer cell killing", Science Direct, vol. 108, Dec. 2016—Abstract Only.

Popp, Ilinca et al "Immune Modulation by Hypofractionated Stereotactic radiation Therapy: Therapeutic Implications", Radiotherapy and Oncology, vol. 120, Issue 2, Aug. 2016,—Abstract Only.

Kang, Josephine et al "Current Clinical trials testing the Combination of Immunotherapy with Radiotherapy", Journal for Immunotherapy of Cancer, vol. 4, 2016.

Victor, Christina Twyman-Saint et al "Radiation and Dual Checkpoint Blockage Activate Non-Redundant Immune Mechanisms in Cancer", Nature, 2015.

Yusuf, Syed Wamique et al "Radiation-Induced heart Disease: A Clinical Update", Cardiology Research and Practice, vol. 2011, Article ID 317659, 2011.

Jabbour, Salma K. et al "Integrating Immunotherapy into Chemoradiation regimens for Medically Inoperable Locally Advanced Non-Small Cell Lung Cancer", Translational Lung Cancer Researcy, vol. 6, No. 2, 2017, pp. 113-118.

Johnson, Douglas B. et al, "Fulminant Myocarditis with Combination Immune Checkpoint Blockade", The New England Journal of Medicine, vol. 375, No. 18, 2016, pp. 1749-1755.

Baban, Babak et al "Upregulation of Programmed Death-1 and Its Ligand in Cardiac Injury Models: Interaction with GADD153", PLOS One, 2015.

Varricchi, Gilda et al "Immune Checkpoint Inhibitors and Cardiac Toxicity: An Emerging Issue", Current Medicinal Chemistry, 2017—Abstract Only.

Laubli, Heinz et al "Acute heart failure due to autoimmune myocarditis under pembrolizumab treatment for metastatic melanoma", Journal for Immunotherapy of Cancer, vol. 3, Article 11, 2015.

Emami, B. "Tolerance of Normal Tissue to Therapeutic Radiation", Reports of Radiotherapy and Oncology, 2013.

Hassel, Jessica C. et al "Combined immune checkpoint blockade (anti-PD-1/anti-CTLA-4): Evaluation and management of adverse drug reactions", Cancer Treatment Reviews, vol. 57, 2017, pp. 36-49.

* cited by examiner

METHODS AND APPARATUS FOR REDUCING RISK TO A SUBJECT UNDERGOING RADIOTHERAPY-BASED TREATMENT

CROSS-REFERENCE TO PRIOR APPLICATIONS

This application is the U.S. National Phase application under 35 U.S.C. § 371 of International Application No. PCT/EP2018/085377, filed on Dec. 18, 2018, which claims the benefit of European Patent Application No. 17209220.7, filed on Dec. 21, 2017. These applications are hereby incorporated by reference herein.

FIELD OF THE INVENTION

This invention relates to the field of radiotherapy-based treatments, and in particular to the field of reducing risk to a subject undergoing a radiotherapy-based treatment or a treatment which includes radiotherapy.

BACKGROUND OF THE INVENTION

Radiotherapy-based treatments expose a subject to risk, and in particular increase a subject's risk to their health. By way of example, it has been recognized that a treatment which combines radiotherapy and immunotherapy can trigger radiation adverse events (AE), such as myocarditis or pneumonitis, despite the treatment's encouraging results in treating cancer.

It is possible to adjust a risk of a radiotherapy-based treatment by adjusting characteristics of the treatment, such as duration, dosage, radiation intensity, radiation spread, and frequency of application. However, adjusting the risk in this manner also alters the efficacy of the radiotherapy-based treatment on a tumor or cancer. For example, the lower the radiation dose of a treatment to a target volume, the lower a reduction in a tumor size. A balance therefore needs to be made between efficacy of treatment and risk to the subject.

There is therefore a desire to accurately quantify a risk a subject may face when undergoing a radiotherapy-based treatment. This will allow for appropriate characteristics of the treatment to be selected which reduces risk to an acceptable level whilst maximizing an efficacy of the treatment. This improves a subject's quality of life and outcome of treatment.

Accurately quantifying a risk will also enable a clinician or subject to make an informed decision as to the likely outcome and risks of a radiotherapy-based treatment. It will also allow preventative measures or actions to be taken to mitigate any predicted or anticipated adverse effects of a treatment.

US 2012/004492 A1 describes a planning processor generating a patient specific adaptive radiation therapy plan based on patient specific biomarkers before and during therapy.

U.S. Pat. No. 9,764,162 B1 describes a treatment planning order component which may include one or more factors associated with a dose of radiation to be prescribed to the patient's tumor.

US 2012/063657 A1 describes a method for therapy monitoring, particularly for diagnosing radiotoxicity and adapting radiotherapy depending on the level of radiotoxicity.

SUMMARY OF THE INVENTION

According to examples in accordance with an aspect of the invention, there is provided a computer-implemented method of generating a radiotherapy-based treatment strategy for a subject undergoing a radiotherapy-based treatment. The method comprises: obtaining a predetermined risk value for the subject; monitoring the subject to identify at least one characteristic of one or more side-effects (also called adverse events) of the radiotherapy-based treatment performed on the subject; modifying the predetermined risk value based on the at least one identified characteristic of the one or more side-effects of the radiotherapy-based treatment; and obtaining a radiotherapy-based treatment strategy based on the modified risk value.

The method proposes to adjust a risk value of a subject based on one or more characteristics of at least one side-effect of a radiotherapy-based treatment. This allows a risk value to be updated based on the response of the subject to a radiotherapy-based treatment. The risk value may therefore be corrected or adjusted to more accurately reflect the characteristics of the subject.

In particular, an initial risk value, being the predetermined risk value, is modified in view of characteristics of one or more side-effects caused by a radiotherapy-based treatment.

By way of example, if a subject responds negatively to a radiotherapy-based treatment (i.e. exhibits significant or hazardous side-effects in organs at risk), a subject's risk value may be increased. On the other hand, if a subject has minimal side-effects to a treatment the subject's risk value may be decreased.

The modified risk value is used to generate a new treatment strategy for the subject. The invention thereby provides a more accurate method of mitigating a risk of a treatment to a subject, by generating or obtaining a suitable treatment strategy for the subject based on an updated and accurate risk value.

The treatment strategy may be selected so as to minimize a risk to the subject (or reduce risk to a maximum acceptable value) whilst maximizing an efficiency of treatment. In particular, the risk value may be used to select appropriate characteristics of a treatment to reduce risk to an acceptable level whilst maximizing treatment efficacy.

The risk value may represent a probability of occurrence of a side-effect within a predetermined time-span during or after the radiotherapy-based treatment or a susceptibility of a subject to a side-effect occurring during or after a radiotherapy treatment. For example, the risk value may represent an occurrence probability of an adverse effect, such as unintended radiation damage, during a radiotherapy-based treatment. The risk value may otherwise represent a relative danger of a predicted adverse effect cause by a radiotherapy-based treatment.

It has been recognised that side-effects will not typically be isolated events but will appear in a cascade of events separated by time. The proposed invention provides an iterative methodology for reassessing the risk to a subject with each passing side-effect. Thus, complex sequences of side-effects may use a reasoning algorithm to help support and advise clinicians in the management of the side-effects.

Preferably, the at least one characteristic comprises at least one temporal characteristic or severity measurement of the one or more side-effects.

Temporal aspects of the side-effects have been shown to accurately reflect a subject's risk to continued or further radiotherapy-based treatment. By assessing the temporal characteristics of side-effects, a risk to the subject may be more accurately determined.

A severity measurement has been shown to provide an accurate representation of a subject's risk to a particular side-effect. In general, the greater the severity of a side-effect, the greater the subject's risk to that side-effect.

Preferably the at least one temporal characteristic comprises one or more of: an on-set time of a side-effect, an occurrence frequency of a side-effect and a duration of a side-effect.

It has been recognized that the more frequent or the more quickly a high-grade or severe side-effect occurs, the more risk a subject may face when undergoing further radiotherapy-based treatment. Adjusting or modifying the risk value based on such considerations therefore provides a more accurate determination of a subject's risk to a radiotherapy-based treatment program.

The predetermined risk value may be formed as an aspect of a risk model representing the risk of a subject to one or more side-effects of one or more treatment strategies. In such a method, the step of obtaining a predetermined risk value comprises obtaining an initial risk model for the subject; the step of modifying the predetermined risk value comprises modifying the initial risk model based on the at least one identified characteristic; and the step of obtaining a radiotherapy-treatment strategy comprises obtaining the radiotherapy-based treatment strategy based on the modified risk model.

Generation of a risk model allows for more accurate, precise and complete characterization of a subject's risk to one or more side-effects. A risk model may represent the risk of a subject to the side-effect(s) for different treatment options. The risk model may otherwise or additionally identify risk values for side-effects in one or more different areas or organs of the subject.

A risk model provides a greater amount of flexibility to determining a subject's likelihood of being affected by a side-effect. This allows for a more bespoke treatment strategy to be generated, leading to improved subject outcome, reduction of hospital re-admissions, and reduced likelihood of a side-effect occurring.

Modifying the risk model may comprise adjusting stored or initial risk model or assigning or obtaining a new risk model to/for the subject.

In an embodiment, the step of obtaining a predetermined risk value for the subject comprises: identifying one or more characteristics of the subject and determining a risk value for the subject based on the identified characteristics of the subject.

The initial risk value for the subject may be determined based on characteristics of that subject. By way of example, demographic information or subject history may be used to estimate or predict a subject's risk to radiotherapy treatment. Determining the initial risk value based on characteristics of the subject provides a more accurate estimate of the risk value, when compared to using a default value.

Preferably, the obtaining predetermined risk value for the subject comprises classifying the subject into a subject class based on the one or more characteristics of the subject; and determining a risk value for the subject based on the subject class of the subject. This provides improved and more accurate characterization of a subject's risk to a side-effect, by classifying the subject into a set of similar subjects.

The step of obtaining the radiotherapy-based treatment strategy optionally comprises: obtaining a radiotherapy treatment strategy corresponding to a radiotherapy-based treatment performed on the subject; and modifying the radiotherapy treatment strategy based on the determined risk value.

Thus, a treatment strategy which has previously been applied to or performed on a subject may be modified based on the determined risk value. By way of example, if the risk value increases, so a radiation dose of the radiotherapy-based treatment strategy may be decreased. The risk value therefore provides a feedback to the radiotherapy-based treatment strategy so that the strategy is adjusted to reflect a response of the subject to the treatment.

The generated strategy is therefore more clinically relevant for a subject, resulting in improved subject outcome and/or quality of life with a reduced risk of adverse effects of the radiotherapy-based treatment occurring.

There is also proposed a computer-implemented method of generating a monitoring plan for a subject undergoing radiotherapy-based treatment. The method comprises: generating a desired radiotherapy-based treatment strategy for a subject by performing the method as previously described; determining the actual radiotherapy-based treatment strategy performed on the subject; and generating a monitoring plan, that can be deployed either in a clinical setting or in a home environment, for the subject based on at least a difference between the desired radiotherapy-based treatment strategy and the actual radiotherapy-based treatment strategy.

In some scenarios, delivery of a radiotherapy-based treatment to a subject may not follow the generated treatment strategy (e.g. due to unaccounted change of the patient body, clinical errors or instrument limitations). Delivery of such a different strategy may alter the risk to a subject, when compared to a predicted risk.

The proposed method generates a monitoring plan for the subject based on the difference between the desired treatment strategy and the actual treatment strategy. By way of example, if an actual radiotherapy-based treatment results in a higher dose of radiation being delivered to a subject when compared to the suggested dose in the desired radiotherapy-based treatment strategy, the monitoring plan may propose to more frequently monitor the characteristics of the subject. The generated monitoring plan therefore enables earlier detection of side-effects (as the risk to a subject has been increased by not following the desired treatment strategy). This result in improved subject outcome, reduced likelihood of adverse side-effects being missed and an initiation of supportive therapeutics.

According to an aspect of the inventive concept there is provided a computer program comprising code means for implementing any previously described method when said program is run on a computer.

According to another aspect of the inventive concept there is provided a treatment planning system for obtaining a radiotherapy-based treatment strategy of for a radiotherapy-based treatment performed on a subject. The treatment planning system is adapted to: obtain a predetermined risk value for the subject; monitor the subject to identify at least one characteristic of one or more side-effects of the radiotherapy-based treatment performed on the subject; modify the predetermined risk value based on the at least one identified characteristic of the one or more side-effects of the radiotherapy-based treatment; and obtain a radiotherapy-based treatment strategy based on the modified risk value.

The at least one characteristic may comprise at least one temporal characteristic or severity measurement of the one or more side-effects.

The treatment planning system may be further adapted to: identify one or more characteristics of the subject; and determine a risk value for the subject based on the identified characteristics of the subject.

There may be provided a radiotherapy-based treatment device adapted to: obtain a radiotherapy-based treatment strategy from a treatment planning system previously described and perform a radiotherapy-based treatment based on the obtained radiotherapy-based treatment strategy.

There may be provided a radiotherapy-based treatment system comprising a treatment planning system as previously described; and a radiotherapy-based treatment device as previously described.

BRIEF DESCRIPTION OF THE DRAWINGS

Examples of the invention will now be described in detail with reference to the accompanying drawings, in which.

DETAILED DESCRIPTION OF THE EMBODIMENTS

According to a concept of the invention, there is proposed a method of generating a strategy for performing a radiotherapy-based treatment and a system for performing the method. During a radiotherapy-based treatment, characteristics (such as occurrence, clinical significance and/or grade) of side-effects are monitored and a risk value modified based on the characteristics. A new treatment strategy for the radiotherapy-based treatment is obtained based on the modified risk value.

Embodiments are at least partly based on the realisation that a subject's risk of adverse side-effects of a radiation treatment may be initially difficult to accurately calculate. Monitoring characteristics of side-effects, such as an on-set time or occurrence frequency of the side-effect, allows for redetermination of a subjects propensity (or risk) to side-effects during a radiotherapy-based treatment. This allows for more accurate determination of an appropriate strategy for treating the subject so as to minimize risk or occurrence of untoward side-effects. Furthermore, non-personalized consensus recommendations or guidelines may be used as a starting point for therapy, which may be modified based on the monitored characteristics.

Illustrative embodiments may, for example, be employed in methods, tools or systems for determining dose target profiles for a radiotherapy-based treatment device. For example, a personalized risk model may be generated for a subject or group of subjects, which allows a treatment strategy to be generated providing an acceptable level of risk whilst maximizing effectiveness of treatment.

The term side-effect, as used herein, refers to any undesirable or unintentional change in the subject's health caused by the radiotherapy-based treatment. An example of a side-effect is the appearance of fulminant myocarditis or radiation-induced pneumonitis.

The term subject, as used herein, refers to any human or animal which undergoes a radiotherapy-based treatment. The term subject may be substituted with the term patient where appropriate.

Figure 1:
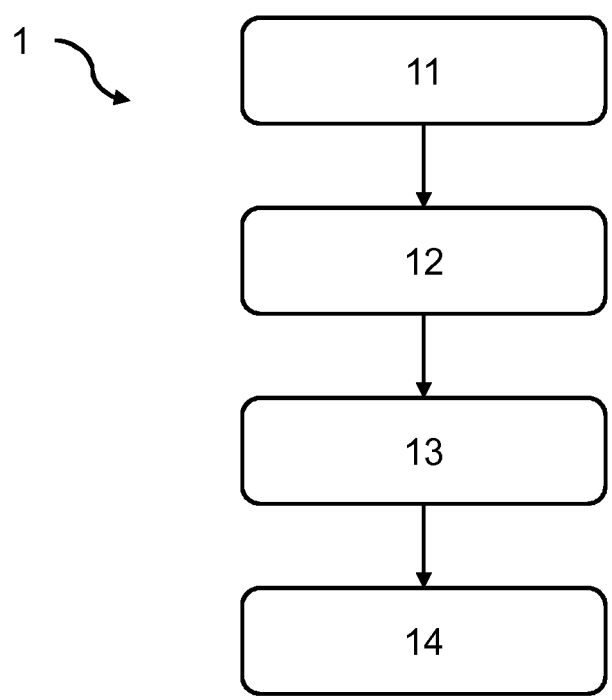
FIG. 1 shows a computer implemented-method of generating a radiotherapy-based treatment strategy according to an embodiment.

FIG. 1 illustrates a computer-implemented method 1 of generating a radiotherapy-based treatment strategy according to a generic embodiment of the invention.

The method 1 comprises a step 11 of obtaining a predetermined risk value for a subject. The predetermined risk value may represent a (predicted) probability that the subject will develop a side-effect, or a propensity of a subject to developing a side-effect, in response to a radiotherapy-based treatment.

Obtaining the predetermined risk value may comprise using a default risk value as the determined risk value. By way of example, a predetermined risk value such as 0.05 may represent a probability of a subject being affected by a particular side-effect. Other methods include using a reported probability (e.g. in the literature) of side-effect occurrence or a reported/predetermined/estimated frequency of occurrence as the predetermined risk value.

The method 1 comprises a step 12 of monitoring the subject to identify at least one characteristic of one or more side-effects of the radiotherapy-based treatment. Preferably, the at least one characteristic comprises a temporal characteristic, such as an onset time, duration or occurrence frequency of a side-effect. In other examples, the at least one characteristic is a grade or severity of the side-effect, e.g. as measured using the Common Terminology Criteria for Adverse Events (CTCAE) guidance.

The method 1 also comprises a step 13 of modifying the predetermined risk value based on the at least one characteristic. In this way, the predetermined risk value is adjusted in view of the subject's reaction to the radiotherapy-based treatment. The adjusted risk value therefore more accurately reflects a subject's propensity to a side-effect.

The method 1 also comprises a step 14 of obtaining a radiotherapy-based treatment strategy based upon the modified risk value. A treatment strategy is therefore obtained or generated based on the more accurate risk value, and may therefore be a more appropriate radiotherapy-based treatment strategy for the subject. Adherence to the generated treatment strategy results in improved subject outcome, with reduced side-effects and with a manageable level of risk.

Preferably, the radiotherapy-based treatment strategy indicates (radiation) dosages to be applied to the subject. The radiation-based treatment strategy may indicate an intensity of radiation, a site of radiation, a duration of radiation, a pattern of radiation, a schedule (including number of fractions or treatment sessions) for applying radiation dosages and so on. Such characteristics may be labelled dose targets, being the intended dosage and radiation delivery scheme to be provided by a treatment device.

Preferably, the radiotherapy-based treatment strategy indicates a non-zero treatment strategy to be performed on the subject. That is, the strategy avoids recommending that no action be taken.

In more complex embodiments, the risk value may be formed as part of a risk model. A risk model may represent one or more subject's overall risk to one or more different side-effects for one or more radiotherapy-based treatment strategies. By way of example, a risk model may comprise a database of different risk values, each risk value representing a predicted tendency of a subject (or subject class) to have a particular side-effect in response to a particular treatment strategy.

The risk model can be used by a radiotherapy planning system as a dose objective/constraint condition, enabling the generation of the best combined immuno-radiotherapy or a chemo-radiotherapy plan that minimizes the occurrence of adverse effects.

The risk model may indicate acceptable or maximum dosage characteristics for a radiotherapy-based treatment in view of the risk to a subject or set of subjects. By way of example, the risk model may indicate that a particular radiation dose is permissible if the subject has no risk, or a very low risk (e.g. p<threshold, where the threshold may be defined by national/international guidelines or specific to local/regional hospital practice) of side-effects occurring for that radiation dose. The risk model may indicate that a different radiation dose is not permissible if the subject is at a high risk of a side-effect occurring (e.g. p>threshold). In this way, an upper limit or bound of permissible dosage characteristics (associated with acceptable levels of risk) may be defined. That is, a risk model may define or constrain allowable treatments strategies that keep risk below an acceptable level.

In particular, the risk model may obtain an acceptable risk value (e.g. p=threshold=0.1), and determine that treatments associated with a risk value above the acceptable risk value are not permitted. The acceptable risk value may be user-defined (by a clinician or subject) or based on standard or ethical medical practices.

In other examples, the risk model provides a set of weights which indicates how characteristics of a radiotherapy-based treatment should be weighted to minimize adverse effects. The weighting may, for example, be a percentage or ratio weighting. For example, if a subject is at a very low risk (e.g. p<0.01) of side-effect occurrence, the risk model may provide a weighting of 1, indicating that any medically-relevant dosage, preferably within non-personalized guidelines, is allowable. The risk model may therefore show a relative risk of side-effect occurrence for different treatment strategies.

The risk model may contain a series of discrete data points, which maps different treatment strategies or particular characteristics of strategies (e.g. intensity/duration of radiation) to different risk values. In other examples, the risk model may instead mathematically model the relationship between characteristics of the radiotherapy-treatment (e.g. radiation intensity/duration) and a risk to the subject. A mathematical model permits the risk of wider range of treatment strategies to be assessed with accuracy.

Data in a risk model may be based on reported or historical instances of side-effect occurrence for a particular treatment strategy, based on standard-of-care clinical practice or clinical trials.

The risk model may further define a risk of a side-effect in a particular area or organ of a subject. That is, a side-effect may be constrained to a particular area or organ of a subject. Thus, the risk model may provide, for each of one or more organs, regions or areas of one or more subjects, a risk or probability of occurrence (i.e. a risk value) of one or more side-effects for one or more different treatment strategies in that area (e.g. radiation dosage or intensity).

The risk model may therefore, for a particular subject, allow identification of a relative risk of one or more side-effects occurring in each of a plurality of regions/areas/organs of the subject for each of a plurality of different radiotherapy-treatments. This provides a detailed map of the various risks of different radiotherapy-treatments which may be used to optimize a radiotherapy-based treatment strategy. By way of example, a radiation intensity may be varied during exposure to different tissues or organs.

Preferably, the risk model comprises different subject classes, profiles, clusters or groups, each associated with a subsidiary risk model. Each subsidiary risk model provides a risk model, such as those previously described, for a particular class of subjects or subject profile. The different subject classes may be associated with different subject characteristics (e.g. age brackets and/or genders) and/or different propensities to side-effects (e.g. high/medium/low risk groups). The subject class may be otherwise labelled a risk group.

The subsidiary risk model of a subject class may define a different risk value for the onset of one or more different side-effects in one or more organs/regions of subjects in that class, for one or more different treatment strategies. The subsidiary risk model of a class may be based on reported or historical instances of side-effect occurrence for a particular treatment strategy for subjects in that class. The subsidiary risk model may contain any information of any other risk model herein described.

Several approaches for obtaining a treatment strategy for a subject using such a risk model are considered.

Figure 2:
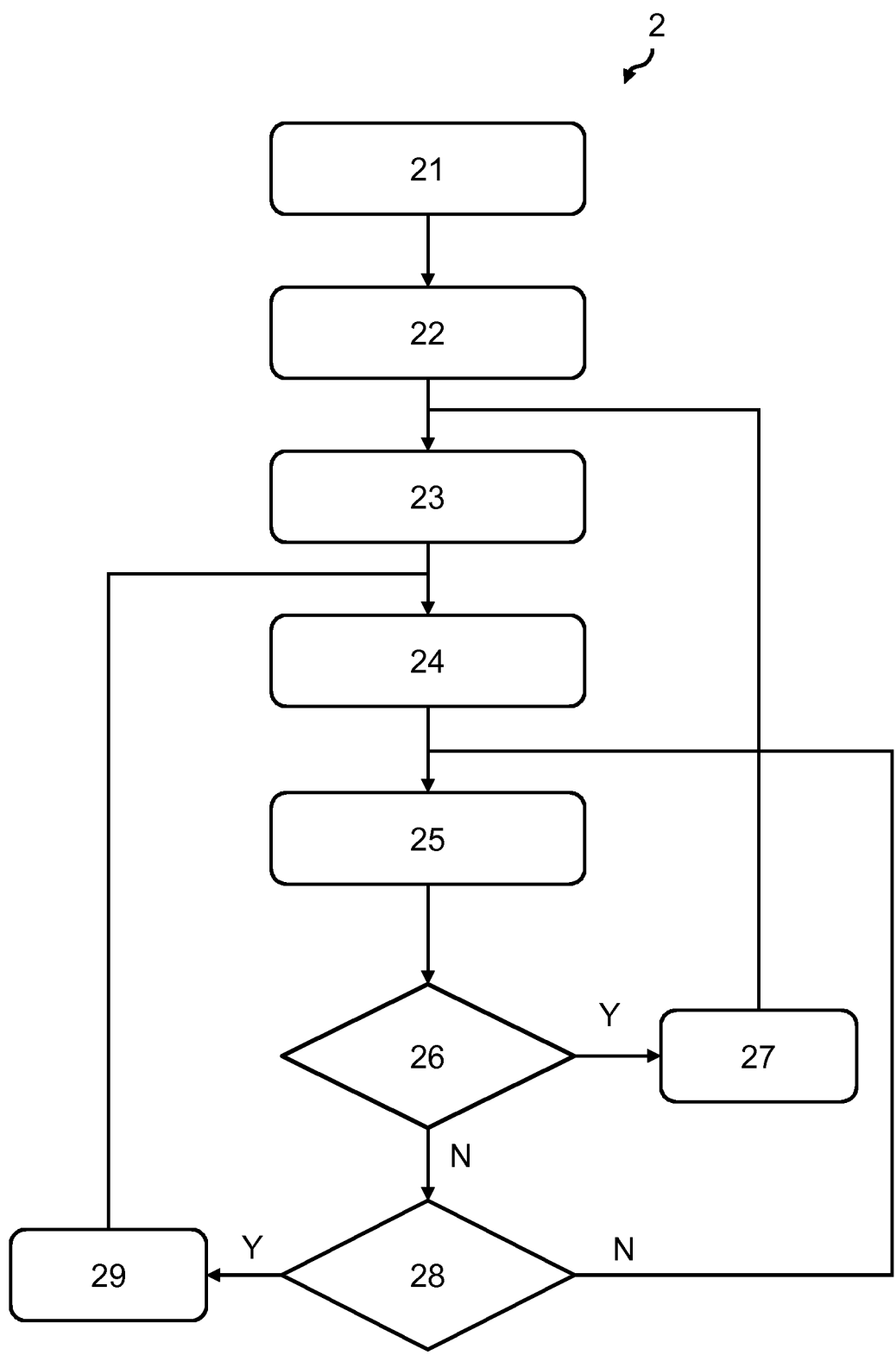
FIG. 2 illustrates a computer-implemented method of obtaining a radiotherapy-based treatment strategy according to another embodiment.

FIG. 2 illustrates a first example of an iterative computer-implemented method 2 of obtaining a treatment strategy for a subject using a risk model.

The method 2 comprises a step 21 of obtaining characteristics of a subject. By way of example, each characteristic may represent a different property of the subject (such as age, gender, smoking status, medical or family history, immunity marker(s), immunity status etc.).

The method 2 comprises a step 22 of assigning or classifying into a subject class or profile based on the obtained characteristics. This classifying may be done according to any known reasoning concept, such ask-nearest neighbors algorithm or a naïve Bayes classification system. In some examples, classification/assignation of a subject in to a class may depend upon entry criteria for each class (such as an age bracket).

Obtaining a risk value/model based on characteristics of a subject provides a more accurate risk value/model of the subject which better represents the subject. This reduces a likelihood of an inappropriate treatment strategy being output by the treatment planning system.

The method 2 comprises a step 23 of obtaining a risk model based on the subject class. By way of example, each subject class may be associated with a different subsidiary risk model which may be selected as the obtained risk model.

The method 2 also comprises a step 24 of obtaining a treatment strategy for the subject based upon the obtained risk model or assigned subject class.

In one example, a subsidiary risk model of a subject class may identify constraints of allowable treatments that keep risk to below an acceptable level. This may be used, in step 24, to restrict the allowable treatment strategies, and the best possible strategy for maximizing efficiency may be selected, e.g. based on historical or reported efficiencies of the available treatments.

In other examples, each subject class could be associated with a different default treatment strategy that attempts to reduce risk of side-effect occurrence to below an acceptable level. The default treatment strategy may be based on best medical practice or historic successes with treatments (e.g. from clinical trials). The step 24 may comprise obtaining this default treatment strategy.

The risk model may identify allowable treatment strategies for a subject (that keep risk below a predetermined or definable value) or identify allowable limits for treatment strategies of the subject, such as a maximum allowable radiation dosage for a session or a recommended number of sessions.

The method 2 comprises a step 25 of monitoring the subject for side-effects. In particular, the step 25 may comprise detecting or obtaining characteristics of side-effects that occur during or following a treatment (within a predetermined time span), which preferably follows the treatment strategy obtained in step 24. Examples of methods of monitoring a subject will be described later.

In steps 26 and 27, the (subsidiary) risk model of a class may be updated based on side-effects detected during a radiotherapy-based treatment. Step 26 comprises determining whether to update the risk model and step 27 comprises updating the risk model.

In one example, if onset of a side-effect is detected before a predicted onset time (e.g. according to previously reported or historic cases), the subsidiary risk model of that class may be adjusted to indicate that subjects in that class are at greater risk of that side-effect than predicted. This adjustment may comprise increasing the relevant risk value in the risk model. This provides a more accurate and up-to-date risk model, reducing the likelihood that an inappropriate or potentially dangerous treatment strategy will be identified.

In a second example, if a severity of a predicted side-effect (e.g. as measured using the CTCAE guidance system) is much greater than predicted, the subsidiary risk model of that class may be adjusted to indicate that subjects in that class are at greater risk of that side-effect.

In steps 28 and 29, the subject may be reclassified based upon characteristics of side-effects that occur during radiotherapy-based treatment or on changes to a subject characteristics due to radiotherapy-based treatment (e.g. change in biomarkers). Step 28 comprises determining whether to reclassify the subject based on (change to) characteristics of side-effects or to the subject. Step 29 comprises reclassifying the subject based on the characteristics.

By way of example, if a side-effect occurs significantly before a predicted onset time or a severity of the side-effect is significantly greater than a predicted severity, the subject may be reassigned into a more conservative class, in which the subsidiary risk model indicates that the subject is at a higher risk of side-effects occurring during treatment or at an earlier predicted onset time.

Step 29 may further comprise altering the entry criteria for a given class in response to this reclassification (e.g. to reflect the new entrant to the class). By way of example, an age bracket or other entrance criteria for a class may be adjusted in step 29 based on the characteristics of the new subject in that class.

The determination of whether to update the risk model and/or reclassify the subject, in steps 26 and 28, may be based on a magnitude of a deviance of a side-effect characteristic from an expected or predicted value. By way of example: no action may be taken if a measured value of a side-effect characteristic is with a first percentage range of the expected/predicted value; a risk model may be updated if a measured value of a side-effect characteristic is between the first percentage range and a second percentage range of the expected/predicted value; and a reclassification of the subject may be performed if a measured value of a side-effect characteristic is outside the second percentage range of the expected/predicted value.

Of course, a new subject class may be generated if a subject does not adhere to the expected response of a subject in any existing classes, or if a new subject does not match the entry criteria for any existing classes. The new subject class may be associated with a default subsidiary risk model or may be assigned a subsidiary risk model of the most similar class.

In some embodiments, the recommended treatment strategy for a class may be adjusted based on the side-effects associated with a treatment applied to a subject of that class. By way of example, a recommended radiation intensity may be decreased if a side-effect occurs more frequently than expected or with greater severity than expected.

Of course, other characteristics of a side-effect may be used to update the risk model. For example, if a frequency of a side-effect occurrence during a treatment is above a predicted value, the risk value associated with that treatment is increased, or the subject is reclassified. In particular, the risk model may store predicted characteristics of side-effects to determine when a treated subject deviates from predicted characteristics (i.e. is at a greater or lower risk of those side-effects). The magnitude of this deviance may be used to modify the predicted risk to a subject in the same class as the treated subject. This concept improves an accuracy and a relevance of the adjustment to the risk value/model for a subject.

In another example, a difference between a predicted severity (e.g. grade) of a side-effect and an actual severity of a characteristic may be used to adjust a risk value in the risk model. In particular, the risk value associated with a particular treatment may be increased and/or the subject reclassified.

The risk value may be adjusted by a predetermined percentage based on a characteristic of a side-effect. For example, if a risk value indicates that a probability of a side-effect occurrence is 0.15, and that side-effect occurs with more severity than predicted, the probability may be increased by 25% (i.e. to 0.1875).

In some embodiments, the characteristics of side-effects of a treated subject are added to a database of treated subjects, their treatments and their side-effects. This database may be processed to predict a risk to a subject to side-effects of a particular treatment.

Thus, there may be provided a reasoning inference algorithm which updates the risk model and/or risk values as more evidence or information becomes available.

In a second example, which is preferably used when no reliable or ab initio data exists for the occurrence of side-effects for different clusters or groups, a risk model is empty (i.e. there exist no classes into which a new subject may be classified). A risk model for a particular subject may be generated using a default set of values/probabilities (e.g. $p=0.1$ or $p=0.05$) or using consensus recommendations or guidelines like the Quantitative Analyses of Normal Tissue Effects in the Clinic (QUANTEC) approach. For example, a QUANIEC approach would predict that a V25<10% of the heart (i.e. where 10% of the volume of the heart receives a radiation dose of 25 Gy) will be associated with a <1% probability of cardiac mortality at 15 years after radiotherapy (i.e. risk value of cardiac mortality at 15 years=0.01). This may be indicated in the risk model.

Other analyses methods for predicting a risk model or risk values for the risk model may be employed where suitable.

As time elapses and the system is used for different subjects, a subject profile population model may be built into the risk model. Thus, for each subject using the system, subject characteristics, treatment information and subject response to the treatment (including side-effect characteristics) may be stored. This stored information may be processed (for example with a Bayesian inference approach) so as to classify the stored subjects into one or more classes, each class being associated with a different risk model based on historical treatments and the occurrence/characteristics of side-effects of subjects receiving those historical treatments in that cluster or group. Algorithms (such as Bayesian algorithms) may cluster subjects based on their responses to certain treatments, and attempt to identify common characteristics of the subjects. New subjects may then be classified into these clusters based on the identified common characteristics, for example, using any previously described method.

In this way, a database of subjects is built, and classes of subjects in the database identified. Future subjects may be therefore be classified according to previously described methods.

Combinations of approaches are possible. For example instead of starting with an empty risk model, one can use biomarkers to stratify subjects with a risk and optimize the stratification by empirical learning in clinical trials.

A risk model may therefore characterize the risk of a plurality of subjects or subject classes/classifications to a plurality of different side-effects for a plurality of different treatment strategies or doses.

Of course, other methods than classification for obtaining a risk value/model are considered. One embodiment uses a look-up table linking historical subject characteristics to recorded or estimated risk values/models. A subject may be matched to a nearest or most similar historical subject, and the associated value/model obtained as the risk value/model for that subject.

Figure 3:
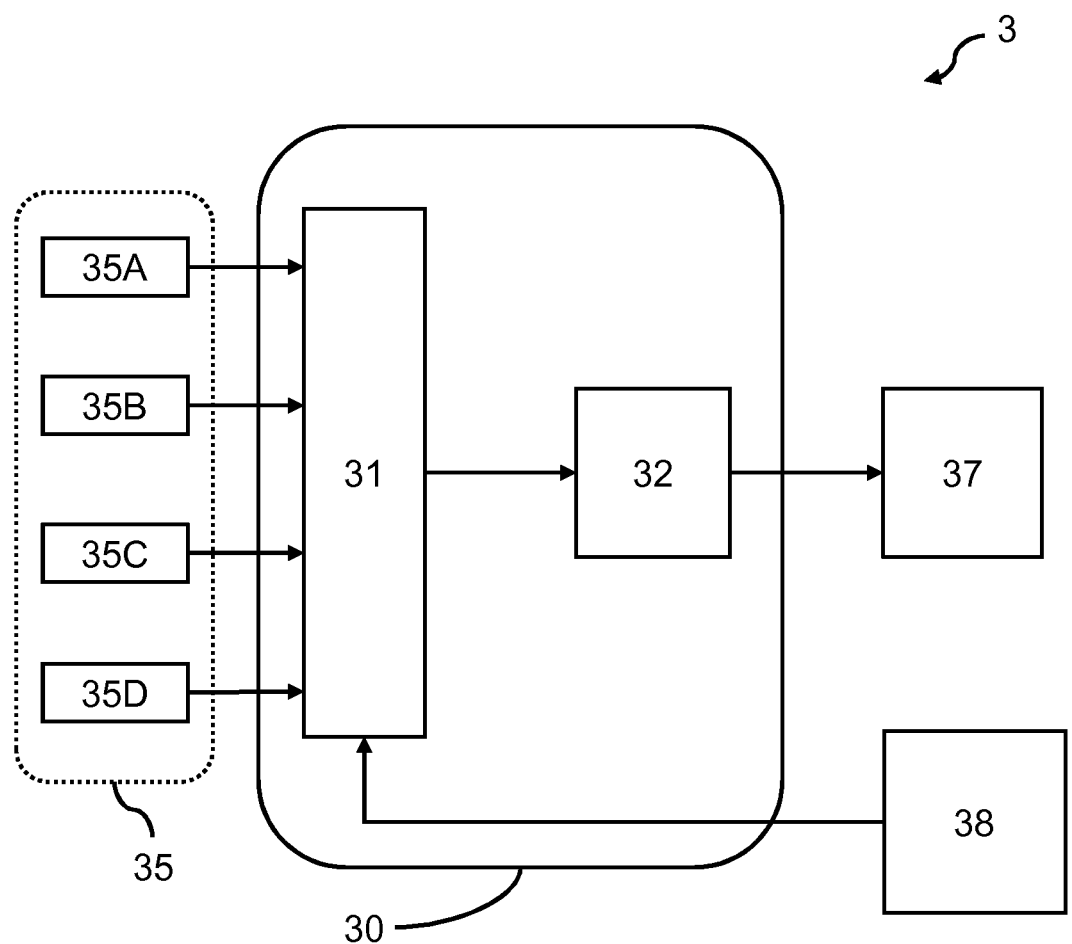
FIG. 3 illustrates a radiotherapy-based treatment system according to an embodiment.

FIG. 3 illustrates a radiotherapy-based treatment system 3 according to an embodiment of the invention. The treatment system 3 comprises a treatment planning system 30 and a radiotherapy-based treatment device 37.

The treatment planning system 30 is adapted to generate/obtain and output a radiotherapy-based treatment strategy. The radiotherapy-based treatment strategy is provided to the radiotherapy-based treatment device 37 for execution.

The radiotherapy-based treatment device 37 is adapted to provide a radiotherapy based treatment (e.g. radiation dosage treatment of a tumor) in accordance with the radiotherapy-based treatment strategy output by the treatment planning system 30. As such, the treatment planning system 30 controls or defines an operation of the radiotherapy-based treatment device 37.

The treatment planning system 30 comprises a risk determination module 31 and a strategy determination module 32. The risk determination module 31 determines a risk value or risk model for a subject (to undergo radiotherapy-based treatment) and the strategy determination module 32 determines a treatment strategy based on the risk value or risk model.

In some examples, the risk determination module initially uses a default risk value/model as the determined risk value/model, such as a reported (in the literature) risk value/model for a subject.

In other examples, and as illustrated in FIG. 3, the risk determination module 31 obtains a set 35 of one or more characteristics 35A-35D of the subject. The risk determination module then generates an initial risk value or risk model on the basis of this set 35. Methods for obtaining a risk value or model based on subject characteristics have been previously described.

The strategy determination module 32 uses the obtained risk value or risk model to determine a treatment strategy for the subject. In particular, the strategy determination module 32 may determine characteristics of a radiotherapy-based treatment to be executed by the radiotherapy-based treatment device.

In an example, the strategy may be based on the subject's risk of developing immune-enhanced, radiation damage-induced adverse events in organs at risk (OARs) in combination therapies involving radiotherapy and checkpoint inhibitor therapies. The dose targets may be provided to the treatment device with the aim of achieving the best plan for, say, tumor control while minimizing the dose provided at organs at risk to reduce radiation triggered immune-mediated adverse events (AE). Other example which could be used in combined chemo-radiotherapy of lung cancer is the selection of a strategy that minimizes the risk of developing esophagitis following irradiation of a tumor in the lung.

For treatment of a tumor, the strategy determination module 32 may determine appropriate dose targets based on the size of the tumor, the fractionation regime (stereotactic body, hypofractionation regimes have different biological effective dose (BED) than standard radiotherapy), time between fractions or treatment sessions and the constraints provided by a risk model obtained by the risk determination module 31 (which may indicate the maximum allowable dose targets in OARs which provide an acceptable level of risk). This allows for determination of a bespoke and individualized treatment strategy, to ensure that a subject receives the most appropriate treatment to maximize their potential outcome.

In another example, based on the restrictions provided by the risk model, the treatment plan can also be adjusted in order to best follow a known or specific fractionation regime (and corresponding dose/fraction By way of example, for a high risk subject it is possible to follow a hypo-fractionation regimes in which the total radiation dose is delivered in concentrated boosts having different biological properties between a tumor (cell kill) and an OAR (healthy tissue with different radiation repair mechanisms in comparison with a tumor). For a lower-risk subject, it may be possible to follow a different strategy, such as a hyperfractionated radiotherapy. For lower-risk subjects, the treatment plan may be experimental or more aggressive, whereas for higher-risk subjects, the treatment plan may be more conservative.

Preferably, the strategy determination module 32 selects the most aggressive treatment strategy for which a risk is below a predetermined or allowable method. The risk model may define the allowable treatments, as previously described, from which the most aggressive (e.g. highest intensity/duration) is selected. This ensures that the most effective available treatment strategy is selected.

Where the risk model defines classes for the subjects, the risk model may define appropriate treatment strategies for each class (e.g. based on symptoms or signs of the subject, such as tumor size, severity or prognosis). Treatment strategies may be based on consensus guidelines or literature from past clinical trials and standard-of-care practice.

As previously described, the risk model may be adjusted as one or more subjects are treated. In these cases, there may be a departure from the initial risk model through creation of new or modified profiles or classes. This may result in a new or modified class which is not associable with any known or recommended guidelines. It is recognized that, traditionally, generation of new guidelines requires a consensus process, which may be lengthy and/or expensive to undertake. The present invention proposes a concept of generating, new, untested treatment strategies to a user.

In one example, a new class may be conceptually located or inserted between two existing classes, with the suggested treatment strategies being an intermediary between those of the two or four most proximate classes (being those classes associated with subjects most similar to the subjects associated with the new class). This may be performed, for example, by taking an average of the characteristics of treatment strategies (e.g. number of treatments, intensity of treatments and so on) of the two or four most proximate classes.

In another example, existing strategies may be extrapolated to reflect the new class. By way of illustration only, consider a scenario where different classes are associated with different ages of a subject, and suggested strategies are increasingly conservative with respect to age. If a new class, associated with subjects of a yet higher age, is provided, that class may be provided with yet more conservative treatment strategies.

It another examples, the treatment strategies of a most proximate class (i.e. that class associated with the most similar subjects to the subjects of the new/modified class) may be taken as the treatment strategies for the new/modified class. Numerous other examples are considered.

Such treatment strategies could be offered to a clinician by way of advice, as they are untested guidelines. In some examples, the clinician could set or adjust the guidelines for a new or modified subject class, e.g. to reflect their own clinical expertise or experience. This may then be advantageously used for future cases which use the proposed treatment planning system.

A subject monitoring device 38 monitors characteristics of side-effects of the radiotherapy treatment performed by the radiotherapy-based treatment device. One example of a subject monitoring device monitors for the appearance of radiation immune-induced myocarditis. Monitored characteristics may include an on-set time, occurrence frequency or duration of a side-effect. These characteristics have been shown to more accurately characterize the risk of a subject to a side-effect.

Several possible clinical tools could be used to detect side-effects and their characteristics. For example, side-effects could identified by a subject's physical symptoms and later confirmed by blood sampling screenings and/or specific imaging procedures (ultrasound, MR, PET/CT imaging). This monitoring technique is particularly advantageous for initial deployment in a home-setting aiming at long-term side-effects, side-effects having a late onset time or side-effects having a low predicted risk of occurrence, as it may be inefficient to continually monitor for such effects within a clinical environment.

It has been recognized that for a combined radiotherapy and immunotherapy approach, the initial manifestations of side-effects are typically non-specific or not easily identified. In such cases a two-fold strategy for monitoring may be required: a systemic blood based for identification of a specific biomarker (which can be performed in the home-setting) and later, should a particular biomarker(s) be identified, a more invasive or more in-depth examination using a medical imaging modality (for example PET/CT). This advantageously provides a clinical tool that monitors a subject without the need for hospital admission, whilst maintaining an extremely high accuracy in identified side-effects. The present invention recognises that certain biomarkers are indicative of particular side-effects.

For example, in radiation accelerated immuno-mediated adverse events, such as PD-L1 upregulated cardiomyopathy induced by radiation, one possible way to detect a side-effect would be monitoring of blood-based inflammatory biomarkers which, upon departing baseline values (e.g. symptomatic of a radiation induced cardiomyopathy), would trigger a specific imaging procedure such as a MR or PET/CT to confirm the onset of side-effects. Such a monitoring system advantageously provides early detection of the onset of side-effects, reducing the probability of a potentially hazardous treatment from continuing (as the treatment strategy will be updated, as described later).

The subject monitoring device 38 passes information about the characteristics of side-effects to the risk determination module 31. The risk determination module 31 uses the characteristics of the side-effects, and optionally the treatment applied to the subject, to modify the (initial) risk value/model, such as any method previously described.

The strategy determination module 32 uses the updated or modified risk value/model to generate a new treatment strategy. For example, a subject may be reclassified, which could affect the treatment strategies available to them (by reason of limiting risk). In this way, the treatment strategy is modified based on the characteristics of side-effects of an earlier treatment strategy. This acts as a form of feedback, and helps to minimize the occurrence of a side-effect in ongoing radiotherapy-based treatment.

In examples, the strategy determination module 31 may obtain a treatment strategy (e.g. the strategy previously used to treat a subject) and modify it in view of the modified risk value/model By way of example, if a risk value of a subject to a side-effect is revised upwards, a recommended intensity or duration of a radiation dose in a treatment strategy is reduced.

Modification of the risk value/model and obtaining a radiotherapy-based treatment strategy may be performed iteratively, such as in accordance with method 2.

Figure 4:
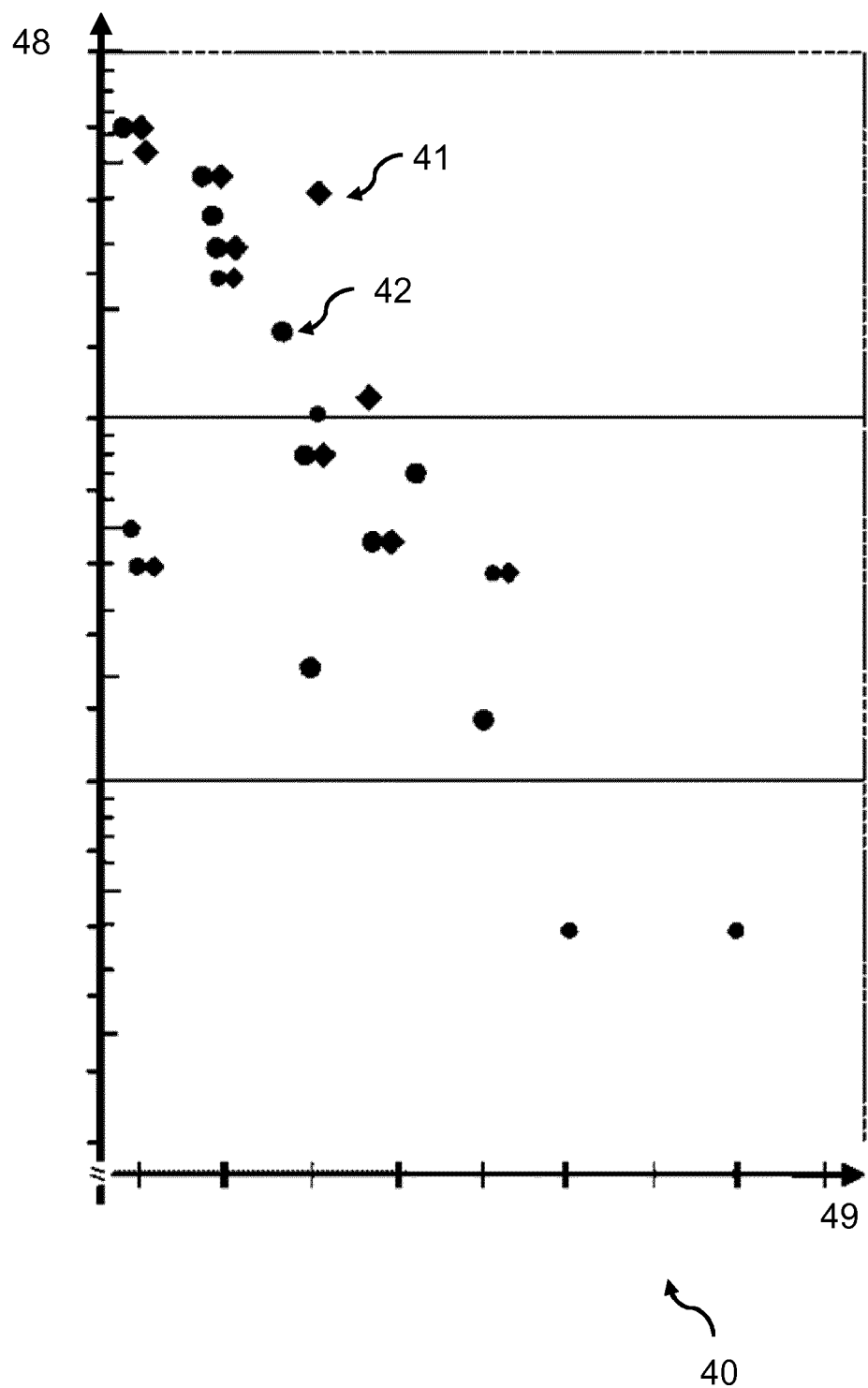
FIG. 4 illustrates a risk model.

FIG. 4 illustrates an example of a risk model 40 for a subject undergoing a certain treatment strategy. The risk model indicates, for different side-effects 41, 42, a probability 48 of occurrence of a side-effect, shown on a logarithmic scale, during the treatment strategy. The risk model 40 also indicates an expected time of onset 49 of the different side-effects. This expected time of onset may be obtained by using historical or reported data as examples.

The expected time of onset may be used as a weight when modifying the risk value/model By way of example, if a particular side-effect occurs at an earlier time (then the expected or predicted time), it may be determined that the subject is at greater risk of that side-effect during radiotherapy-based treatment, and the relevant risk value may be adjusted accordingly. The difference between expected time of side-effect on-set and actual time of side-effect on-set may advantageously be used to more accurately characterize a subject's risk or susceptibility to that side-effect. The greater the difference, the greater the subject's risk.

In another approach, the time before onset of a side-effect may be similar to an expected time, but the grade or severity of the side-effect may be significantly greater and therefore more serious or life-threating. This would require more aggressive clinical management. Thus, in examples, the greater the difference of a severity of the side-effect, the more a magnitude of a risk value associated with that side-effect is modified.

Further embodiments of the method provide steps for generating a monitoring plan or surveillance plan for the subject. The monitoring plan may specify when characteristics of one or more side-effects should be checked, sensed or otherwise obtained. To generate the monitoring plan, a risk model identifying an expected time of on-set or occurrence of a side-effect should be used. The monitoring plan may identify that the subject is to be monitored for a particular side-effect (e.g. a skin immune-mediated side-effect) when that side-effect is expected to appear.

The monitoring plan may be used by the subject monitoring device to schedule when readings, sensor data, observations or surveys (either lead by clinical staff or selfreported by the subject) should be acquired. This allows for automated acquisition of side-effect characteristics, without continual monitoring being required. This improves an efficiency of monitoring a subject. In other embodiments, the monitoring plan is presented to a user (e.g. via an audiovisual output) for execution.

However, it has been recognized that actual treatment of a subject may not be able to adhere to the treatment strategy, for example, due to technical reasons and limitations. This may affect the characteristics of side-effects. By way of example, if a higher dose of radiation is applied to a subject than recommended by the treatment strategy, side-effects may occur earlier than anticipated.

Figure 5:
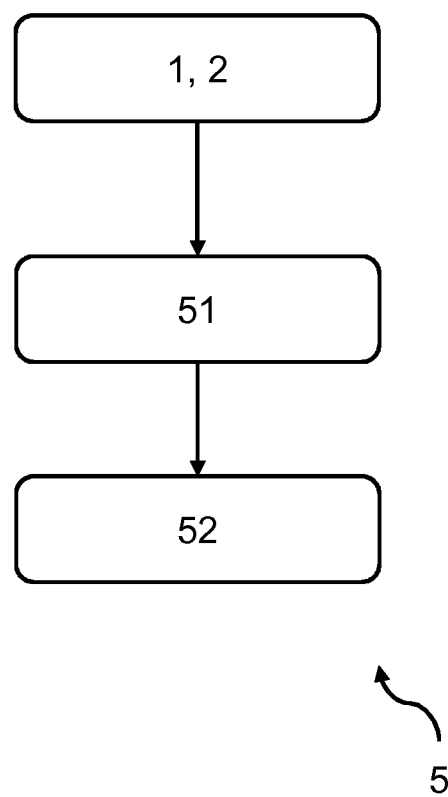
FIG. 5 illustrates a method of generating a monitoring plan for a subject undergoing radiotherapy-based treatment according to an embodiment.

FIG. 5 illustrates a computer-implemented method 5 of generating a monitoring plan in such a scenario.

The method 5 comprises a step of performing the method 1, 2 of generating a desired or recommended radiotherapy treatment strategy as previously described.

The method 5 further comprises a step 51 of determining the actual radiotherapy-based treatment strategy performed on the subject. Information about the actual radiotherapy-based treatment strategy may be obtained from the radiotherapy-based treatment device, via a user input or via a treatment monitoring device.

The method 5 further comprises a step 52 of generating a monitoring plan based on a difference between the actual treatment strategy and the desired/recommended treatment strategy. This ensures that the occurrence, onset, or other characteristic of side-effects is not missed when following the monitoring plan.

By way of example, if an actual radiotherapy-based treatment is associated with a higher intensity/duration than recommended by the treatment strategy, it may be expected that the onset of a side-effect will occur earlier than anticipated by the risk model. The monitoring plan may therefore recommend performing additional or earlier checks for the characteristics of a side-effect that can be stored as an option in the hospital EMR (Electronic Medical Records) and be assessable by the clinical staff in the hospital or general practitioner.

Described embodiments are particularly advantageous for a treatment which includes a combination of radiotherapy and immunotherapy. This is because there are significant radiation adverse effects which are triggered by this combination, such adverse effects having a particular need of mitigation to prevent their emergence.

A risk model may explicitly include the synergistic effects of radiation damage and immune response induced by the following systemic therapy. That is, a risk model may be directed towards radiotherapy and immunotherapy based treatments.

The present invention has described some examples of generating a treatment strategy based on a risk model, in particular using the risk model to identify, for a given subject, allowable treatment strategies or allowable limits for characteristics of a treatment strategy (e.g. treatment frequency, treatment intensity and so on). Other methods of using a risk model to develop a treatment strategy would be readily appreciated by the skilled person.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Further aspects of the invention are defined by the following clauses. Each of the clauses defines independently patentable subject matter.

1. A computer-implemented method (1, 2) of generating a radiotherapy-based treatment strategy for a subject undergoing a radiotherapy-based treatment, the method comprising:
   obtaining (11, 23) a predetermined risk value for the subject;
   monitoring (12, 25) the subject to identify at least one characteristic of one or more side-effects of the radiotherapy-based treatment performed on the subject;
   modifying (13, 27) the predetermined risk value based on the at least one identified characteristic of the one or more side-effects of the radiotherapy-based treatment; and
   obtaining (14, 24) a radiotherapy-based treatment strategy based on the modified risk value.

2. The computer-implemented method of clause 1, wherein the at least one characteristic comprises at least one temporal characteristic or severity measurement of the one or more side-effects.

3. The computer-implemented method of clause 2, wherein the at least one temporal characteristic comprises one or more of: an on-set time of a side-effect, an occurrence frequency of a side-effect, severity of side/adverse events and a duration of a side-effect.

4. The computer-implemented method of any preceding clause, wherein the predetermined risk value is formed as an aspect of a risk model representing the risk of a subject to one or more side-effects of one or more treatment strategies, and wherein:
   the step of obtaining a predetermined risk value comprises obtaining (23) an initial risk model for the subject;
   the step of modifying the predetermined risk value comprises modifying (27) the initial risk model based on the at least one identified characteristic; and
   the step of obtaining (24) a radiotherapy-treatment strategy comprises obtaining the radiotherapy-based treatment strategy based on the modified risk model.

5. The computer-implemented method of any preceding clause, wherein the obtaining a predetermined risk value for the subject comprises:
   identifying (21) one or more characteristics of the subject; and
   determining a risk value for the subject based on the identified characteristics of the subject.

6. The computer-implemented method of clause 5, wherein the obtaining a predetermined risk value for the subject comprises:
   classifying (22) the subject into a subject class based on the one or more characteristics of the subject; and
   determining (23) a risk value for the subject based on the subject class of the subject.

7. The computer-implemented method of any preceding clause, wherein the obtaining the radiotherapy-based treatment strategy comprises:
   obtaining a radiotherapy treatment strategy corresponding to a radiotherapy-based treatment performed on the subject; and
   modifying the radiotherapy treatment strategy based on the determined risk value.

8. A computer-implemented method of generating a monitoring plan for a subject undergoing radiotherapy-based treatment, the method comprising:
  generating (1, 2) a desired radiotherapy-based treatment strategy for a subject by performing the method according to any preceding clause;
  determining (51) the actual radiotherapy-based treatment strategy performed on the subject; and
  generating (52) a monitoring plan for the subject based on at least a difference between the desired radiotherapy-based treatment strategy and the actual radiotherapy-based treatment strategy.
9. The computer-implemented method of any preceding clause, wherein the side-effect is the occurrence of an immune-mediated radiation adverse event.
10. A computer program comprising code means for implementing the computer-implemented method of any one of any preceding clause when said program is run on a computer.
11. A treatment planning system (30) for obtaining a radiotherapy-based treatment strategy of for a radiotherapy-based treatment performed on a subject, the treatment planning system being adapted to:
  obtain a predetermined risk value for the subject;
  monitor the subject to identify at least one characteristic of one or more side-effects of the radiotherapy-based treatment performed on the subject;
  modify the predetermined risk value based on the at least one identified characteristic of the one or more side-effects of the radiotherapy-based treatment; and
  obtain a radiotherapy-based treatment strategy based on the modified risk value.
12. The treatment planning system of clause 11, wherein the at least one characteristic comprises at least one temporal characteristic or severity measurement of the one or more side-effects.
13. The treatment planning system of any of clauses 11 or 12, further adapted to:
  identify one or more characteristics of the subject; and
  determine a risk value for the subject based on the identified characteristics of the subject.
14. A radiotherapy-based treatment device (37) adapted to:
  obtain a radiotherapy-based treatment strategy from a treatment planning system (30) according to any of clauses 11 to 13; and
  perform a radiotherapy-based treatment based on the obtained radiotherapy-based treatment strategy.
15. A radiotherapy-based treatment system (3) comprising:
  a treatment planning system (30) according to any of clauses any of clauses 11 to 13; and
  a radiotherapy-based treatment device (37) according to clause 14.

The invention claimed is:
1. A computer-implemented method of generating a radiotherapy-based treatment strategy for a subject undergoing a radiotherapy-based treatment, the method comprising:
  obtaining a risk model for the subject, the risk model representing a risk of a subject class to a plurality of side-effects for a plurality of radiotherapy-based treatment strategies;
  monitoring the subject to identify at least one characteristic of one or more side-effects of the radiotherapy-based treatment performed on the subject;
  modifying the risk model based on the at least one identified characteristic of the one or more side-effects of the radiotherapy-based treatment; and
  obtaining a radiotherapy-based treatment strategy based on the modified risk model identifying constraints for allowable treatment strategies.
2. The computer-implemented method of claim 1, wherein the risk model comprises a set of weights which indicates how characteristics of a radiotherapy-based treatment should be weighted to minimize adverse effects.
3. The computer-implemented method of claim 1, wherein the risk model contains a series of discrete data points which maps different radiotherapy-based treatment strategies or particular characteristics of said strategies to different risk values.
4. The computer-implemented method of claim 1, wherein data in the risk model is based on reported or historical instances of side-effect occurrence for a particular radiotherapy-based treatment strategy.
5. The computer-implemented method of claim 1, wherein the risk model further defines a risk of a side-effect in a particular area or organ of the subject class.
6. The computer-implemented method of claim 1, wherein the at least one characteristic comprises at least one temporal characteristic or severity measurement of the one or more side-effects.
7. The computer-implemented method of claim 6, wherein the at least one temporal characteristic comprises one or more of: an on-set time of a side-effect, an occurrence frequency of a side-effect, severity of side/adverse events and a duration of a side-effect.
8. The computer-implemented method of claim 7, wherein the obtaining a risk model for the subject comprises:
  identifying one or more characteristics of the subject; and
  classifying the subject into a subject class based on the one or more characteristics of the subject; and
  determining the risk model for the subject based on the subject class of the subject.
9. The computer-implemented method of claim 1, wherein the risk model indicates an expected on-set time of different side-effects, wherein the at least one characteristic comprises an actual on-set time of a side-effect, and wherein the risk model is modified based on a difference between the expected on-set time of the side-effect and the actual on-set time of the side-effect.
10. A computer-implemented method of generating a monitoring plan for a subject undergoing radiotherapy-based treatment, the method comprising:
  generating a desired radiotherapy-based treatment strategy for a subject by performing the method according to any preceding claim;
  determining the actual radiotherapy-based treatment strategy performed on the subject; and
  generating a monitoring plan for the subject based on at least a difference between the desired radiotherapy-based treatment strategy and the actual radiotherapy-based treatment strategy.
11. The computer-implemented method of claim 10, wherein the side-effect is the occurrence of an immune-mediated radiation adverse event.
12. A computer program comprising code means for implementing the computer-implemented method of claim 10 when said program is run on a computer.

13. A treatment planning system for obtaining a radiotherapy-based treatment strategy of for a radiotherapy-based treatment performed on a subject, the treatment planning system being adapted to:
- obtain a risk model for the subject, the risk model representing a risk of a subject class to a plurality of side-effects for a plurality of radiotherapy-based treatment strategies;
- monitor the subject to identify at least one characteristic of one or more side-effects of the radiotherapy-based treatment performed on the subject;
- modify the risk model based on the at least one identified characteristic of the one or more side-effects of the radiotherapy-based treatment; and
- obtain a radiotherapy-based treatment strategy based on the modified risk model identifying constraints for allowable treatment strategies.

14. A radiotherapy-based treatment device adapted to:
obtain a radiotherapy-based treatment strategy from a treatment planning system according to claim 13; and
perform a radiotherapy-based treatment based on the obtained radiotherapy-based treatment strategy.

15. A radiotherapy-based treatment system comprising:
a treatment planning system; and
a radiotherapy-based treatment device according to claim 14.

* * * * *